United States Patent [19]

Schutzer

[11] Patent Number: 5,201,769
[45] Date of Patent: Apr. 13, 1993

[54] HIP STEM WITH PROXIMAL BUILD-UP BLOCKS

[76] Inventor: Steven F. Schutzer, 85 Seymour St., Hartford, Conn. 06106

[21] Appl. No.: 764,342

[22] Filed: Sep. 23, 1991

[51] Int. Cl.⁵ .......................... A61F 2/36; A61F 2/30
[52] U.S. Cl. ........................................ 623/23; 623/18; 623/20
[58] Field of Search ...................... 623/16, 18, 20, 22, 623/23

[56] References Cited

U.S. PATENT DOCUMENTS

| 4,012,796 | 3/1977 | Weisman et al. | 623/18 |
| 4,731,086 | 3/1988 | Whiteside et al. | 623/20 |

FOREIGN PATENT DOCUMENTS 0393425 10/1990 European Pat. Off. .............. 623/22

OTHER PUBLICATIONS

Seipe, Journal of Bone and Joint Surgery, Mar. 1991, pp. 31, 32, 33.
Lima Int. Corp. Journal of Bone and Joint Surgery, Sep. 1991, p. 77.

Primary Examiner—Ronald Frinks
Attorney, Agent, or Firm—Sherman and Shalloway

[57] ABSTRACT

A prosthetic hip stem implant with U-shaped buildup block that can be selectively connected to the hip stem adjacent to the flange to augment the height of the prosthesis. The buildup block will be available in three heights to accommodate for varying degrees of bone loss as determined intraoperatively.

7 Claims, 2 Drawing Sheets 5,201,769

HIP STEM WITH PROXIMAL BUILD-UP BLOCKS

FIELD OF THE INVENTION

This invention relates to the femoral component of a hip prosthesis that will have the option of modular proximal augmentation for restoration of femoral length in patients with bone loss or certain fractures.

BACKGROUND OF THE INVENTION

In situations where there has been loss of bone in the proximal femur, conventional components may not suffice. In addition, certain hip fractures may be treated with an implant that replaces the proximal femur. During the procedure, the surgeon may find that there is not enough bone remaining to use a standard prosthesis. Oftentimes radiographic pictures do not indicate the degree of bone loss and in general lack bone quality information which can be critical to the fit of the prosthesis. In addition, not infrequently, the surgeon may need to resect additional bone to reach satisfactory bone stock. In such circumstances the standard prostheses available and even custom implants constructed on the basis of the preoperative radiographs may not precisely fit the remaining bone in an optimum matter and therefore cannot be used.

SUMMARY OF THE INVENTION

This femoral component can virtually eliminate these problems by providing the option of using one of three buildup blocks which may be selected intraoperatively and secured to the stem if required. The buildup blocks are stepped in 10 mm increments in height and are generally U-shaped in cross-section. The blocks are connected to the stem by two screws. A rib or keel extends downward from a flange of the femoral component and seats within a groove on the buildup blocks to prevent rotation and provide alignment between the implant and the block. The lower surface of the buildup block includes a rib or keel which engages a groove on the resected end of the bone. The buildup block will be either 10 mm or 20 mm or 30 mm high to allow the surgeon to intraoperatively adjust to the ideal height.

Accordingly, it is an object of the invention to provide for a novel hip stem prosthesis.

Another object of the invention is to provide for a hip stem with proximal buildup blocks.

Still another object of the invention is to provide for a novel hip stem prosthesis having buildup blocks with a mating keel and groove to prevent rotation therebetween.

Further objects of the invention will become apparent upon a reading of the following description taken with the accompanying drawings.

DESCRIPTION OF THE PREFERRED EMBODIMENT

Figure 1:
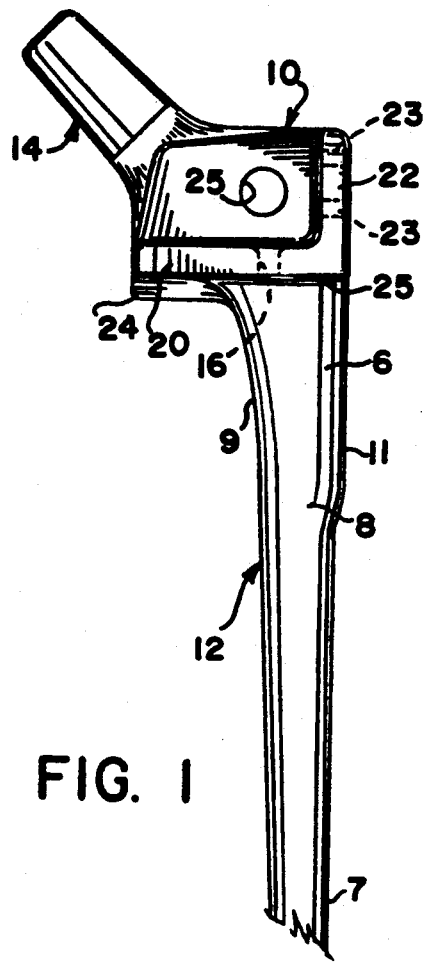
FIG. 1 is a fragmented side elevation view of the hip stem implant of the invention without a buildup block.

The preferred embodiment herein disclosed is not intended to be exhaustive or to limit the invention to the precise forms disclosed. Rather, it is chosen and described so that others skilled in the art may utilize it teachings.

The present invention is directed to a hip implant 10 comprising a first portion including a neck 14 and a second portion including a stem 12 with a flange 20 extending outwardly from a junction of said first portion and said second portion. A distal portion of the stem is provided for seating within an intramedullary canal of a bone. A buildup block having a predetermined height is provided, connected adjacent to the flange and to the second portion of the implant. The buildup block contacts the flange 20 and the proximal end 6 of stem 12 to space the first portion of the implant a predetermined distance from the bone and a predetermined distance from the proximal end 6 of the stem 12.

Figure 2:
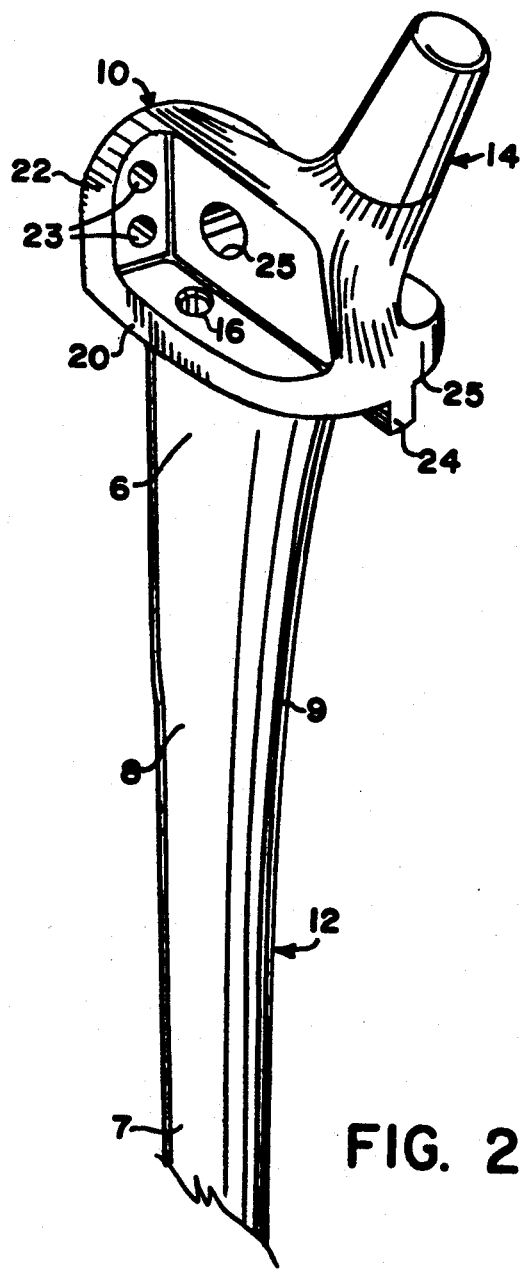
FIG. 2 is a fragmented perspective view of the hip stem implant of the invention without a buildup block.
Figure 3:
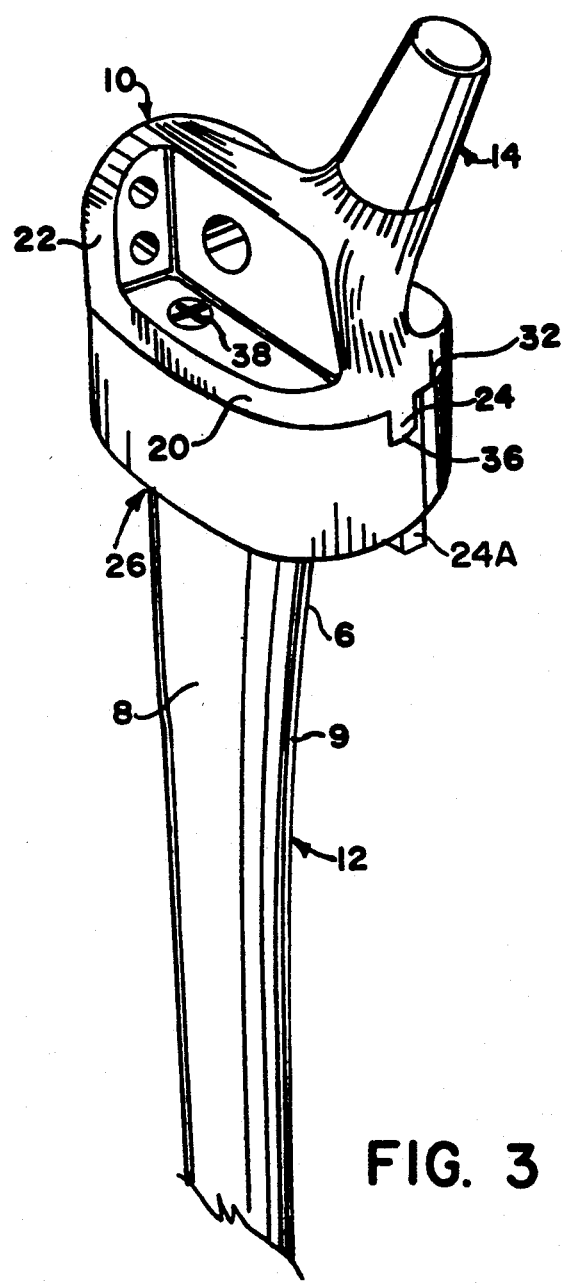
FIG. 3 is a perspective view of the hip stem prosthesis with a buildup block attached.

Referring now to FIGS. 1-3, hip stem implant 10 is illustrated as including a generally longitudinal stem 12 and a neck 14 integrally extending in an angular orientation well known in the art. Stem 12 of implant 10 includes a proximal end 6, a distal end 7 (partially shown), and a pair of approximately opposite sidewalls 8 separated by a medial wall 9 and a lateral wall 11. A flange 20 extends integrally from the proximal end 6 of the hip stem of the stem 12 and is generally transverse to the stem. Flange 20 is generally U-shaped which, as illustrated, extends along the sidewalls 8 and medial wall 9 of hip stem 10. A rear flange 22 extends integrally along a proximal portion of the lateral wall 11 generally transverse to flange 20. A through bore 16 extends through flange 20 on each side of neck 14 to accommodate a screw for connection of the buildup block 26 (discussed below). A rib or keel 24 extends outwardly from medial wall 9 along the bottom surface 25 of flange 20. Two suture holes 23 are formed through rear flange 22 to accommodate suture wires for attachment of soft tissue and muscle during surgery. A bore, not shown, formed through the neck of the implant provides access for a known removal tool to pull the implant from the bone during test fitting of the prosthesis.

Figure 5:
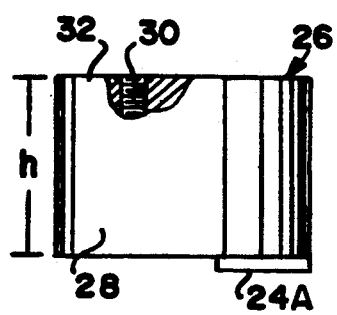
FIG. 5 is a top view of a buildup block of the invention.
Figure 4:
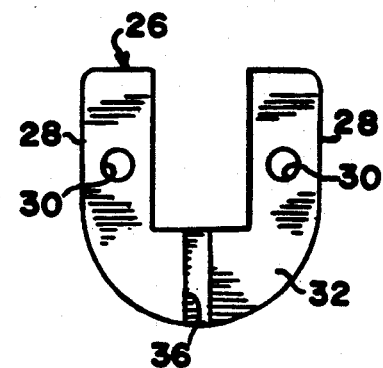
FIG. 4 is a side view of the buildup block of the invention with portions sectioned for illustrative purposes.

An example of a buildup block 26 is illustrated in FIGS. 3-5. Each buildup block 26, only one shown, is generally U-shaped and has a defined height "h" (see FIG. 5). A threaded blind bore 30 extends from upper surface 32 into each leg 28 of buildup block 26. A groove 36 is formed in the upper surface 32 at a location generally midway between the legs 28. A rib or keel 24A extends downwardly from the lower surface of buildup block 26 midway between each leg 28.

If the surgeon determines that augmentation of the bone is required to achieve a proper post operative leg length and prosthesis fit, a buildup block 26 of an appropriate height "h" (either 10 mm, 20 mm or 30 mm) is connected to the stem 10 by a pair of screws 38 (only one shown) traversing bores 16 of flange 20 and turned within threaded blind bores 30 of buildup block 26. The upper surface 32 of buildup block 26 contacts the bottom surface 25 of flange 20. Keel 24 of hip stem 10 seats within groove 36 of the buildup block. When the stem of the implant with buildup block is inserted into the medullary canal of the femur (not shown), the lower or distal surface of the buildup block contacts the femur about the medullary canal. Keel 24A seats within a groove cut in the proximal end of the bone (not shown) to aid in preventing rotation of the implant relative to the bone. By choosing between the three buildup blocks of varying heights "h" the surgeon can properly compensate for the loss of bone stock and maintain the patients normal leg length.

It should be understood that the buildup block may be formed with a wide variety of heights "h" and that the stem can be used without any of the buildup blocks. In the preferred embodiment, three buildup blocks 26 will be available during the surgical procedure such that the surgeon may intraoperatively connect the appropriately sized buildup block to the hip stem. Once the buildup block is connected to the hip stem, the unit may be implanted into the patient in a known manner not discussed here.

Finally, it should be understood that the invention is not to be limited to the precise form disclosed but may be modified within the scope of the appended claims.

We claim:

1. A prosthetic implant having a first portion including a neck and a second portion including a stem, with a flange extending outwardly from a junction of said first and second portions, said stem extending longitudinally away from said flange and comprising a distal portion for seating within an intramedullary canal of a bone, and a buildup block having a predetermined height, wherein said flange includes a keel extending downward from a lower surface of said flange, said buildup block includes a groove formed in an upper surface thereof, said flange keel being accommodated within said buildup block groove with said buildup block connected to said flange and said surfaces in contact with one another, and said buildup block for contacting said bone to space said first portion of said implant a predetermined distance from said bone.

2. The implant of claim 1 wherein said buildup block is generally U-shaped in cross-section.

3. The implant of claim 1 wherein said buildup block further includes a keel extending downwardly from said buildup block for engagement with a proximal groove in said bone.

4. The implant of claim 1 wherein the height of the buildup block is 10 to 30 mm.

5. A buildup block for a prosthetic hip stem implant, said implant including a stem portion and a neck portion with an integral flange at their junction, said flange extending transverse to said stem and including a lower surface and a keel extending downward from said lower surface, said buildup block including a groove formed in an upper surface thereof, said flange keel being accommodated within said buildup block groove with said buildup block connected to said flange and said surfaces in contact with one another, said buildup block defining a height "h" between upper and lower surfaces of said buildup block, said buildup block being adapted for connection to said hip stem to define a predetermined height from the lower surface of said buildup block to the lower surface of said flange.

6. The buildup block of claim 5 wherein said buildup block further includes a keel extending downwardly from said buildup block for engagement with a proximal groove in said bone.

7. The buildup block of claim 5 wherein the height of the buildup block is 10 to 30 mm.

* * * * *